(12) United States Patent
Limem et al.

(10) Patent No.: US 12,390,326 B2
(45) Date of Patent: *Aug. 19, 2025

(54) IMPLANT WITH FILLABLE RESERVOIR (71) Applicant: Tepha, Inc., Lexington, MA (US)

(72) Inventors: Skander Limem, Lynnfield, MA (US);
Fabio Felix, Foxborough, MA (US);
Said Rizk, Windham, NH (US); David
P. Martin, Arlington, MA (US); Simon
F. Williams, Cambridge, MA (US)

(73) Assignee: Tepha, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/538,903

(22) Filed: Dec. 13, 2023

(65) Prior Publication Data
US 2024/0130854 A1  Apr. 25, 2024

Related U.S. Application Data (60) Division of application No. 17/679,995, filed on Feb. 24, 2022, now Pat. No. 11,883,279, which is a
(Continued)

(51) Int. Cl.
A61F 2/18 (2006.01)
A61F 2/00 (2006.01)
(Continued)

(52) U.S. Cl.
CPC ............ *A61F 2/186* (2013.01); *A61F 2/0059* (2013.01); *A61L 27/54* (2013.01); *A61L 27/58* (2013.01);
(Continued)

(58) Field of Classification Search
None
See application file for complete search history.

(56) References Cited

U.S. PATENT DOCUMENTS 5,733,336 A    3/1998  Neuenfeldt et al.
7,371,400 B2 *  5/2008  Borenstein ............. B29C 65/02
                                                    435/395
(Continued)

FOREIGN PATENT DOCUMENTS

EP        1750615 A2     2/2007
WO    WO 2017/120608 A1  7/2017

OTHER PUBLICATIONS

International Search Report and Written Opinion mailed Apr. 17, 2019 for International Application No. PCT/US2018/061793.
(Continued)

Primary Examiner — Dominic Lazaro
(74) Attorney, Agent, or Firm — Wolf, Greenfield & Sacks, P.C.

(57) ABSTRACT

Implants with fillable reservoirs have been developed that are suitable for rhinoplasty, breast reconstruction, ear reconstruction, and replacement, reconstruction or repair of other soft tissues. The implants can be filled with graft material prior to implantation. The implants are preferably made from resorbable polymers, can be tailored to provide different geometries, mechanical properties and resorption rates in order to provide more consistent surgical outcomes. The implants preferably have an interconnected network of unit cells with microporous outer layers and optionally some or all of the unit cells having at least one macropore in their outer layers. The implants can be loaded by injection with microfat, collagen, DCF, cells, bioactive agents, and other augmentation materials, prior to implantation.

20 Claims, 7 Drawing Sheets

Related U.S. Application Data continuation of application No. 16/195,144, filed on Nov. 19, 2018, now Pat. No. 11,291,539.

(60) Provisional application No. 62/587,859, filed on Nov. 17, 2017.

(51) Int. Cl.
*A61L 27/54* (2006.01)
*A61L 27/58* (2006.01)
*A61F 2/12* (2006.01)

(52) U.S. Cl.
CPC ............ *A61F 2/12* (2013.01); *A61F 2002/183* (2013.01); *A61F 2210/0061* (2013.01); *A61F 2250/0003* (2013.01)

(56) References Cited

U.S. PATENT DOCUMENTS

| | | | |
|---|---|---|---|
| 7,641,688 B2 * | 1/2010 | Lesh | A61F 2/0059 623/23.72 |
| 11,291,539 B2 * | 4/2022 | Limem | A61L 27/54 |
| 2009/0162276 A1 | 6/2009 | Martin et al. | |
| 2011/0309541 A1 | 12/2011 | Thompson et al. | |
| 2012/0150285 A1 | 6/2012 | Cahil et al. | |
| 2014/0277572 A1 | 9/2014 | Martin et al. | |
| 2015/0230917 A1 | 8/2015 | Hristov et al. | |
| 2019/0151081 A1 | 5/2019 | Limem et al. | |
| 2022/0387171 A1 | 12/2022 | Limem et al. | |

OTHER PUBLICATIONS

Gorbet et al., Endotoxin: the uninvited guest. Biomaterials. Dec. 2005;26(34):6811-17.

Lim, A Review of Spun Bond Process. J Textile Apparel Tech Management. Apr. 8, 2010;6(3):1-13.

Williams et al., Poly-4-hydroxybutyrate (P4HB): a new generation of resorbable medical devices for tissue repair and regeneration. Biomed Tech. Oct. 2013;58(5):439-52.

* cited by examiner

IMPLANT WITH FILLABLE RESERVOIR

CROSS-REFERENCE TO RELATED APPLICATIONS

This application is a divisional of U.S. application Ser. No. 17/679,995, filed Feb. 24, 2022, which is a continuation of U.S. application Ser. No. 16/195,144, filed Nov. 19, 2018, which claims the benefit of and priority to U.S. Provisional Application No. 62/587,859, filed Nov. 17, 2017. The contents of these applications are incorporated herein by reference in their entirety.

FIELD OF THE INVENTION

The present invention generally relates to the field of surgery, and more particularly, the invention relates to implants with reservoirs that can be filled with augmentation material, such as fat, microfat, collagen, gels, hydrogels, and bioactive agents. The reservoir of the implant comprises a microporous outer layer and either an interconnected network of unit cells, or the edges of the microporous outer layer have been sealed. The reservoir can be filled with graft material and bioactive agents prior to implantation or post-implantation. The implant may optionally comprise macroporous fiber structure inside the fillable reservoir, and may also optionally comprise one or more macropores in the outer microporous layer. The implants are suitable for use where space filling is required in the human anatomy, in particular rhinoplasty, ear, facial and breast reconstruction.

BACKGROUND OF THE INVENTION

Rhinoplasty is a complex procedure requiring the alteration of underlying nasal structures such as bone, cartilage, ligaments and soft tissue. It may be undertaken for a variety of reasons, including (i) improving aesthetic appearance of the patient's nose; (ii) restoring structure and shape following trauma; (iii) correcting abnormalities of the nose; and (iv) correcting functional problems of the nasal passage to improve breathing. Regardless of the reasons for rhinoplasty, the surgeon seeks to create or preserve certain proportions between various parts of the nose and face in order to restore or maintain functionality, remediate structural issues, and address aesthetic factors.

Augmentation of the nasal dorsum, to build up the bridge of the nose, is a common rhinoplasty procedure used to treat patients with collapsed or flat noses, or to change the appearance of a relatively low bridge, common in certain ethnic groups, to a more projected, pronounced, or "Western" profile.

One preferred method to augment the dorsum involves the use of diced cartilage fascia (DCF). The use of DCF is often preferred to solid grafts of autologous costal cartilage because the solid grafts can warp, and also because they have limited availability when long, straight grafts are needed. In contrast. DCF may be obtained, for example, from cartilage of the rib, ear, or septum. The cartilage is chopped into very small pieces, typically about 0.5 to 1 mm cubes. Rib cartilage is a particularly abundant source of autologous cartilage graft material. To augment the dorsum, the DCF is placed inside a small pouch made from an autologous fascia (commonly temporalis fascia), the pouch is manually sealed using sutures, and inserted onto the dorsum by the surgeon. This approach provides greater flexibility in shape and size, and reduces the risk of warping when compared to solid grafts. The use of a pouch material for the DCF prevents uncontrolled dispersion of the cartilage fragments, reduces palpability and improves appearance (relative to use of DCF without a pouch).

Materials that have been used to form a pouch for DCF include Surgicel® (Ethicon, San Lorenzo), an oxidized regenerated cellulose hemostat, AlloDerm® (LifeCell, Bridgewater), an acellular tissue allograft derived from cadaver skin, and deep temporal fascia autograft. However, each of these materials has their challenges. The Surgicel and AlloDerm products have been associated with cartilage resorption, and the use of temporal fascia, harvested from tissue in the temple region of the head, results in increased operating time, and produces morbidity at a second surgical site. It has also been reported that temporal fascia can lack consistency, has a tendency to shrink, has poor dimensional stability, and that harvesting of temporal fascia can create the risk of alopecia. Moreover, it is not possible to easily control the degradation rate, three-dimensional geometry, or thickness of harvested tissues, or incorporate bioactive agents into harvested tissues. Therefore, there is still a need for improved rhinoplasty implants.

An implant for use in rhinoplasty, particularly a reservoir that can be filled with microfat, fat, fat extracts, cells, gels, hydrogels, or other biological material, that does not need to be harvested from the patient and that can be engineered with a desired thickness and shape, including three-dimensional shapes, would be particularly desirable. For example, an implant that could be formed in a range of sizes, including different thicknesses, to address palpability issues and other facial contouring needs would be very desirable. Preferably, the implant is able to act as a wick to take up, for example, microfat, fat, fat extracts, cells, stem cells, collagen, and other biological materials, and help prevent loss of these materials from the implant. It would also be highly desirable for the implant to allow tissue-ingrowth, particularly when the thickness of the implant is greater than 1 mm, and for the implant to have a tunable rate of degradation leading to complete degradation. Ideally, it would also be desirable for the implant to comprise bioactive agents, including, but not limited to, growth factors and antibiotics that can improve the performance of the implant and the surgical outcome. It would also be desirable if the implant could be used in other procedures, such as ear reconstruction and breast augmentation and reconstruction, as well as the repair or reconstruction of soft tissue.

It is therefore an object of the invention to provide an implant with a fillable reservoir.

It is another object of the invention to provide an implant with a fillable reservoir that can be filled with microfat, fat extracts, fat, cells, diced cartilage, DCF, gels, hydrogels, and other bioactive agents and materials.

It is still another object of the invention to provide an implant with a fillable reservoir, wherein the implant allows tissue ingrowth and is resorbable.

It is yet another object of the invention to provide an implant with a fillable reservoir, wherein the shape and size of the implant can be engineered, and the implant can be cut and shaped.

It is a still further object of the invention to provide methods to fill the implant, and methods to use the implant in rhinoplasty, ear and breast reconstruction, and other soft tissue implantation and augmentation procedures.

SUMMARY OF THE INVENTION

Implants with a fillable reservoir have been developed that are suitable for use in rhinoplasty, ear and breast reconstruction, and repair, reconstruction, or replacement of other soft tissues. The implants eliminate the need to harvest temporalis fascia, transverse rectus abdominis myocutaneous (TRAM) tissue, or other tissues that are used to make graft material or pouches, and inconsistencies associated with the use of harvested biological tissues. The fillable reservoir is made from an outer microporous layer with either an interconnected network of unit cells or by sealing the edges of the microporous layer, wherein the implant may optionally have at least one macropore. The implants may further comprise macroporous fiber structure inside the implant, and may also further comprise additional microporous layers within the implant. The reservoir may be filled with grafting material, such as microfat, fat, fat extracts, cells, stem cells, collagen, DCF, gels, hydrogels, bioactive agents, and other substances useful in rhinoplasty and other reconstruction or repair procedures. Preferably, the microporous layers are made from polymers and engineered to act as wicks that can take up and retain graft materials, such as microfat, fat extracts, and other substances useful in rhinoplasty and other reconstructive procedures. The polymers are preferably degradable with a tunable rate of degradation, and are designed to allow tissue in-growth.

Also disclosed is a method of filling the reservoirs of the implants prior to implantation. The method includes filling the reservoir of the implant using a needle and syringe. The implants can be filled, for example, with microfat, fat, fat extracts, cells, stem cells, gels, hydrogels. DCF, fascia, dermis, cartilage, and other substances useful in rhinoplasty, breast and ear reconstruction, and other soft tissue repair and reconstruction procedures. Methods to implant the implants are also disclosed.

DETAILED DESCRIPTION OF THE INVENTION

It would be desirable to have a rhinoplasty implant that the surgeon can use to create or restore certain proportions between various parts of the nose and face in order to restore or maintain functionality, remediate structural issues, and address aesthetic factors. Ideally, the implant can be engineered with a desired shape, and constructed to minimize the need to harvest tissues from the patient which can result in morbidity at the donor site as well as increase operating time. Furthermore, it would be highly desirable for the implant to permit tissue in-growth, degrade in a controlled manner, and be replaced over time with the patient's own tissue. The use of an implant with a fillable reservoir, made from an interconnected network of unit cells comprising microporous outer layers with some or all of the cells having at least one macropore, could however allow the surgeon to implant any desired shape, optionally containing graft or other materials, preferably autologous graft, and permit the implant to be replaced with the patient's own tissues if the implant is made of resorbable materials. The implant would preferably be formable or moldable by hand into a desired shape, minimize the need to harvest tissues from the patient, and provide the surgeon with a desirable means to deliver microfat, fat, fat extracts, cells, stem cells, gels, hydrogels, bioactive agents, and other materials to the implant site. If desired, the surgeon could cut the implant to further customize the shape and size of the implant. And, the implant could be used not only in rhinoplasty procedures, but also in other plastic surgery procedures, such as ear and breast reconstruction [for example, as a TRAM (transverse rectus abdominis myocutaneous) flap substitute], and other soft tissue repair, reconstruction, and replacement procedures.

I. Definitions

"Absorbable" as generally used herein means the material is degraded in the body, and the degradation products are eliminated or excreted from the body. The terms "absorbable", "resorbable", "degradable", and "erodible", with or without the prefix "bio", can be used interchangeably herein, to describe materials broken down and gradually absorbed, excreted, or eliminated by the body, whether degradation is due mainly to hydrolysis or mediated by metabolic processes.

"Average pore size diameter" as used herein is calculated using open source ImageJ software available at https://imagej.nih.gov/ij/index.html.

"Bioactive agent" is used herein to refer to therapeutic, prophylactic or diagnostic agents, preferably agents that promote healing and the regeneration of host tissue, and also therapeutic agents that prevent, inhibit or eliminate infection. "Agent" includes a single such agent and is also intended to include a plurality.

"Biocompatible" as generally used herein means the biological response to the material or device being appropriate for the device's intended application in vivo. Any metabolites of these materials should also be biocompatible.

"Blend" as generally used herein means a physical combination of different polymers, as opposed to a copolymer formed of two or more different monomers.

"Copolymers of poly-4-hydroxybutyrate" as generally used herein means any polymer containing 4-hydroxybutyrate with one or more different hydroxy acid units.

"Diced cartilage fascia" ("DCF") as generally used herein means cartilage obtained, for example, from the rib, ear, or septum, that has been chopped into very small pieces.

"Elongation to break" as used herein means the increase in length of a material that occurs when tension is applied to break the material. It is expressed as a percentage of the material's original length.

"Endotoxin units" as used herein are determined using the limulus amebocyte lysate (LAL) assay as further described by Gorbet et al. Biomaterials, 26:6811-6817 (2005).

"Macroporous" materials or structures as used herein have average pore size diameters of at least 75 microns.

"Microfat" as generally used herein means fat obtained from an area of the body, including the abdomen, thighs, buttocks or waist area, usually by making a small incision and using a small cannula to suction it from the body, and processed to remove blood cells and reduce the liquid content of the aspirate.

"Microporous" materials or structures as generally used herein have average pore size diameters of less than 10 microns.

"Molecular weight" as used herein, unless otherwise specified, refers to the weight average molecular weight (Mw), not the number average molecular weight (Mn), and is measured by GPC relative to polystyrene.

"Poly-4-hydroxybutyrate" as generally used herein means a homopolymer containing 4-hydroxybutyrate units. It can be referred to herein as Tepha's P4HB™ polymer or TephaFLEX® biomaterial (manufactured by Tepha, Inc., Lexington. MA).

"Suture pullout strength" as used herein means the peak load (kg) at which an implant fails to retain a suture. It is determined using a tensile testing machine by securing an implant in a horizontal plate, threading a suture in a loop through the implant at a distance of 1 cm from the edge of the implant, and securing the suture arms in a fiber grip positioned above the implant. Testing is performed at a crosshead rate of 100 mm/min, and the peak load (kg) is recorded. The suture is selected so that the implant will fail before the suture fails. The suture pullout strength may be converted and expressed as Newtons.

Figure 7:
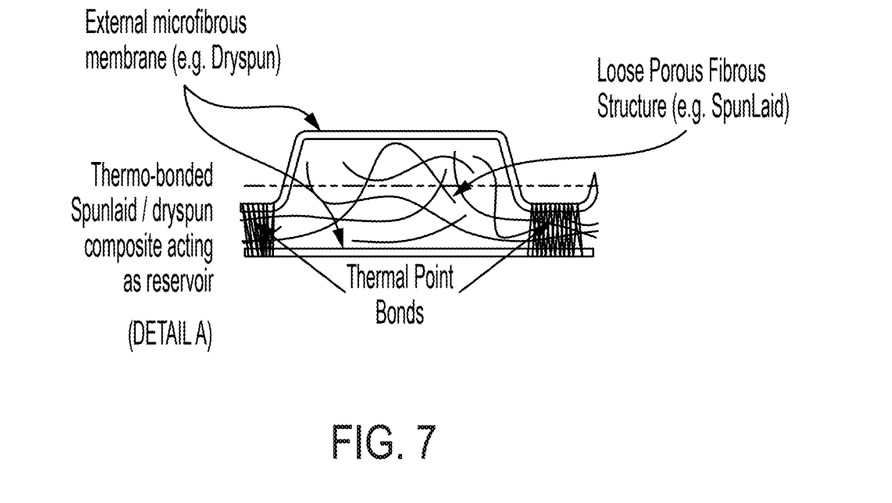
FIG. 7 is a diagram showing the cross-section of a thermally-bonded fillable reservoir of an implant that is part of an interconnected network of unit cells comprising a microporous outer layer and a macroporous inner layer formed from fibers.

"Unit cell" as generally used herein means a small compartment. An example of a unit cell cross-section is shown in FIG. 7. The compartment may be empty or contain a filler.

II. Materials for Preparing Implants with Fillable Reservoirs

Implants with fillable reservoirs have been developed. The implants can optionally be filled with augmentation materials such as microfat, fat, fat extracts, collagen, gels, hydrogels, DCF, cells, stem cells, as well as bioactive agents, prior to implantation. The shapes and sizes of the implants can be tailored to meet the individual needs of the patient, and the implants can allow tissue in-growth and preferably are made of degradable polymers with a tunable rate of degradation. The implants so formed preferably have a pyrogen level of less than 20 endotoxin units per device.

A. Polymers for Preparing Implants with Fillable Reservoirs

The implants with fillable reservoirs may comprise permanent materials, such as non-degradable thermoplastic polymers, including polymers and copolymers of ethylene and propylene, including ultra-high molecular weight polyethylene, ultra-high molecular weight polypropylene, nylon, polyesters such as poly(ethylene terephthalate), poly(tetrafluoroethylene), polyurethanes, poly(ether-urethanes), poly(methylmethacrylate), polyether ether ketone, polyolefins, and poly(ethylene oxide). However, the implants preferably comprise degradable materials, and more preferably are made completely from degradable materials. In a preferred embodiment, the implants are made from one or more absorbable polymers, preferably absorbable thermoplastic polymers and copolymers. The implant may, for example, be prepared from polymers including, but not limited to, polymers of glycolic acid, lactic acid, 1,4-dioxanone, trimethylene carbonate, 3-hydroxybutyric acid, 4-hydroxybutyrate, ε-caprolactone, including polyglycolic acid, polylactic acid, polydioxanone, polycaprolactone, copolymers of glycolic and lactic acids, such as VICRYL® polymer, MAXON® and MONOCRYL® polymers, and including poly(lactide-co-caprolactones); poly(orthoesters); polyanhydrides; poly (phosphazenes); polyhydroxyalkanoates; synthetically or biologically prepared polyesters; polycarbonates; tyrosine polycarbonates; polyamides (including synthetic and natural polyamides, polypeptides, and poly(amino acids)); polyesteramides; poly(alkylene alkylates); polyethers (such as polyethylene glycol, PEG, and polyethylene oxide, PEO); polyvinyl pyrrolidones or PVP; polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); silk (including recombinant silks and silk derivatives and analogs); chitin; chitosan; modified chitosan; biocompatible polysaccharides; hydrophilic or water soluble polymers, such as polyethylene glycol, (PEG) or polyvinyl pyrrolidone (PVP), with blocks of other biocompatible or biodegradable polymers, for example, poly (lactide), poly(lactide-co-glycolide, or polycaprolcatone and copolymers thereof, including random copolymers and block copolymers thereof. Preferably the absorbable polymer or copolymer will be substantially resorbed after implantation within a 1 to 24-month timeframe, and retain some residual strength for at least 2 weeks to 2 months.

Blends of polymers, preferably absorbable polymers, can also be used to prepare the rhinoplasty implants. Particularly preferred blends of absorbable polymers are prepared from absorbable polymers including, but not limited to, polymers of glycolic acid, lactic acid, 1,4-dioxanone, trimethylene carbonate, 3-hydroxybutyric acid, 4-hydroxybutyrate, ε-caprolactone or copolymers thereof.

In a particularly preferred embodiment, poly-4-hydroxybutyrate (Tepha's P4HB™ polymer, Lexington, MA) or a copolymer thereof is used to make the implant. Copolymers include P4HB with another hydroxyacid, such as 3-hydroxybutyrate, and P4HB with glycolic acid or lactic acid monomer. Poly-4-hydroxybutyrate is a strong, pliable thermoplastic polyester that is biocompatible and resorbable (Williams, et al. Poly-4-hydroxybutyrate (P4HB): a new generation of resorbable medical devices for tissue repair and regeneration. *Biomed. Tech.* 58(5):439-452 (2013)). Upon implantation, P4HB hydrolyzes to its monomer, and the monomer is metabolized via the Krebs cycle to carbon dioxide and water. In a preferred embodiment, the P4HB homopolymer and copolymers thereof have a weight average molecular weight, Mw, within the range of 50 kDa to 1,200 kDa (by GPC relative to polystyrene) and more preferably from 100 kDa to 600 kDa. A weight average molecular weight of the polymer of 50 kDa or higher is preferred for processing and mechanical properties.

B. Additives

Certain additives may be incorporated into the implant, preferably in the absorbable polymer, copolymer or blends thereof that are used to make the implant. Preferably, these additives are incorporated during a compounding process to produce pellets that can be subsequently melt-processed. For example, pellets may be extruded into fibers suitable for making the implants. In another embodiment, the additives may be incorporated using a solution-based process, for example, fibers may be spun from solutions of the polymer and one or more additives. In a preferred embodiment, the additives are biocompatible, and even more preferably the additives are both biocompatible and resorbable.

In one embodiment, the additives may be nucleating agents and/or plasticizers. These additives may be added in sufficient quantity to produce the desired result. In general, these additives may be added in amounts between 1% and 20% by weight. Nucleating agents may be incorporated to increase the rate of crystallization of the polymer, copolymer or blend. Such agents may be used, for example, to facilitate fabrication of the implant, and to improve the mechanical properties of the implant. Preferred nucleating agents include, but are not limited to, salts of organic acids such as calcium citrate, polymers or oligomers of PHA polymers and copolymers, high melting polymers such as PGA, talc, micronized mica, calcium carbonate, ammonium chloride, and aromatic amino acids such as tyrosine and phenylalanine.

Plasticizers that may be incorporated into the compositions for preparing the implants include, but are not limited to, di-n-butyl maleate, methyl laureate, dibutyl fumarate, di(2-ethylhexyl) (dioctyl) maleate, paraffin, dodecanol, olive oil, soybean oil, polytetramethylene glycols, methyl oleate, n-propyl oleate, tetrahydofurfuryl oleate, epoxidized linseed oil, 2-ethyl hexyl epoxytallate, glycerol triacetate, methyl linoleate, dibutyl fumarate, methyl acetyl ricinoleate, acetyl tri(n-butyl) citrate, acetyl triethyl citrate, tri(n-butyl) citrate, triethyl citrate, bis(2-hydroxyethyl) dimerate, butyl ricinoleate, glyceryl tri-(acetyl ricinoleate), methyl ricinoleate, n-butyl acetyl rincinoleate, propylene glycol ricinoleate, diethyl succinate, diisobutyl adipate, dimethyl azelate, di(n-hexyl) azelate, tri-butyl phosphate, and mixtures thereof. Particularly preferred plasticizers are citrate esters.

C. Bioactive Agents

The implants can be loaded, for example using a needle and syringe, or coated with bioactive agents. Bioactive agents may be included in the implants for a variety of reasons. For example, bioactive agents may be included in order to improve tissue in-growth into the implant, to improve tissue maturation, to provide for the delivery of an active agent, to improve wettability of the implant, to prevent infection, and to improve cell attachment. The bioactive agents may also be incorporated into the structure of the implant.

The implants may contain cellular adhesion factors, including cell adhesion polypeptides. As used herein, the term "cell adhesion polypeptides" refers to compounds having at least two amino acids per molecule that are capable of binding cells via cell surface molecules. The cell adhesion polypeptides include any of the proteins of the extracellular matrix which are known to play a role in cell adhesion, including fibronectin, vitronectin, laminin, elastin, fibrinogen, collagen types I, II, and V, as well as synthetic peptides with similar cell adhesion properties. The cell adhesion polypeptides also include peptides derived from any of the aforementioned proteins, including fragments or sequences containing the binding domains.

The implants can incorporate wetting agents designed to improve the wettability of the surfaces of the implant structures to allow fluids to be easily adsorbed onto the implant surfaces, and to promote cell attachment and or modify the water contact angle of the implant surface. Examples of wetting agents include polymers of ethylene oxide and propylene oxide, such as polyethylene oxide, polypropylene oxide, or copolymers of these, such as PLURONICS®. Other suitable wetting agents include surfactants or emulsifiers.

The implants can contain gels, hydrogels or living hydrogel hybrids to further improve wetting properties and to promote cellular growth throughout the thickness of the scaffold. Hydrogel hybrids consist of living cells encapsulated in a biocompatible hydrogel like gelatin, methacrylated gelatin (GelMa), silk gels, and hyaluronic acid (HA) gels.

The implants can contain active agents designed to stimulate cell in-growth, including growth factors, cellular differentiating factors, cellular recruiting factors, cell receptors, cell-binding factors, cell signaling molecules, such as cytokines, and molecules to promote cell migration, cell division, cell proliferation and extracellular matrix deposition. Such active agents include fibroblast growth factor (FGF), transforming growth factor (TGF), platelet derived growth factor (PDGF), epidermal growth factor (EGF), granulocyte-macrophage colony stimulation factor (GMCSF), vascular endothelial growth factor (VEGF), insulin-like growth factor (IGF), hepatocyte growth factor (HGF), interleukin-1-B (IL-1 B), interleukin-8 (IL-8), and nerve growth factor (NGF), and combinations thereof.

Other bioactive agents that can be incorporated in the implants include antimicrobial agents, in particular antibiotics, disinfectants, oncological agents, anti-scarring agents, anti-inflammatory agents, anesthetics, small molecule drugs, anti-angiogenic factors and pro-angiogenic factors, immunomodulatory agents, and blood clotting agents. The bioactive agents may be proteins such as collagen and antibodies, peptides, polysaccharides such as chitosan, alginate, hyaluronic acid and derivatives thereof, nucleic acid molecules, small molecular weight compounds such as steroids, inorganic materials such as hydroxyapatite, or complex mixtures such as platelet rich plasma. Suitable antimicrobial agents include: bacitracin, biguanide, trichlosan, gentamicin, minocycline, rifampin, vancomycin, cephalosporins, copper, zinc, silver, and gold. Nucleic acid molecules may include DNA, RNA, siRNA, miRNA, antisense or aptamers.

The implants may also contain allograft material and xenograft materials, including acellular dermal matrix material and small intestinal submucosa (SIS).

In yet another preferred embodiment, the implants may incorporate systems for the controlled release of the therapeutic or prophylactic agents.

D. Microporous Layers

Microporous layers suitable for making the outer layers of the implant are preferably non-woven and may be produced, for example, by spun laying, solution spinning, including dry spinning, centrifugal spinning and electro-spinning, and melt blowing. The microporous layers have average pore size diameters that are less than ten microns (10 μm). The microporous layers may be produced from the polymers listed in Section II.A. The microporous layers are preferably made from resorbable polymers.

A suitable equipment set up for preparing spunlaid microfiber outer layers for the implant includes an extruder, metering pump, die assembly, spinning zone, fiber drawing and deposition system, and a collecting belt, bonding zone and winder (Lim H., A review of spun bond process, *JTATM*, 6:1-13, (2010)). The spunlaid microfiber outer layers may be produced by conveying polymer extrudate via a filter and metering pump to the die assembly, and extruding the polymer through spinneret holes. This process may be accomplished by melt spinning, dry spinning or wet spinning, but melt spinning is preferred. A preferred spinneret for melt spinning has 40-220 nozzles with individual nozzle diameters ranging from 120 to 160 microns. The extruded filaments exiting the spinneret are preferably quenched, for example using cool air, and are then attenuated by feeding the filaments into a tapered conduit using preferably high velocity air. In alternative embodiments, the filaments may be attenuated using take-up rolls or with electrostatic methods. After attenuation, the filaments are collected on a moving belt to form a web of microporous fibers, preferably using a vacuum to aid collection. Prior to collection on the belt, the filaments may be separated using mechanical force, aerodynamic force, or electrostatic charge using processes such as mechanical oscillation, electrostatic charging, slot attenuators, air foils, full-width draw rolls and centrifugal foaming. The filaments in the web may then be bonded, for example, by hydroentangling, thermal or chemical means, or by needle punching. A particularly preferred method of bonding the collected web is point-thermal bonding which bonds small regions of the collected web using temperature and pressure to fuse fibers, and provides a flexible spunlaid microfiber structure suitable for use as the outer layer of the implant. The collected web may also be point bonded using ultrasonic spot welding, for example, by placing an ultrasonic horn over a calendaring roll with nips to create point bonds. Prior to bonding, the collected web may, if desired, be calendered using calendering rolls.

In a preferred embodiment, spunlaid layers suitable for use in the rhinoplasty implants are made from P4HB and copolymers thereof. Suitable spunlaid P4HB (weight average molecular weight of 50 kDa to 600 kDa) may be produced using extrusion temperatures of 60° C. to 250° C. more preferably 80° C. to 230° C. and even more preferably maximum extrusion temperatures of 210-230° C. At these temperatures, it is possible to collect P4HB spunlaid wherein the spunlaid consists of a loose network of P4HB fibers with some slight fiber-to-fiber surface bonding due to the surface stickiness of the P4HB fibers when deposited on the collecting belt. Increased fiber-to-fiber bonding may be achieved using a vacuum system with an air flow rate ranging from between 40 and 220 cu ft/min (1.13-6.23 m³/min).

Dry spun microfiber outer layers suitable for making the implants may be produced from a polymer solution by pumping the solution through a spinneret with numerous holes. A suitable equipment set up comprises a source of compressed gas, preferably air, a regulator to control the gas pressure, an inline heater to control compressed air temperature, a pump drive to control the injection rate of the polymer solution, a spinneret with multiple holes through which the polymer solution is pumped, and a collector, preferably a collector that can rotate. The microfiber layers are produced by dissolving the polymer in a volatile solvent and pumping the polymer solution through a spinneret, allowing the solvent time to evaporate so that fibers solidify from the solution and can be collected as a micro-fibrous nonwoven. Properties of the dry spun nonwoven may be optimized by controlling the concentration of the polymer in the solution, the solvent type, the weight average molecular weight of the polymer, type of polymer, gas pressure, the distance between the spinneret and the collector, and the movement of the collector, if any.

In a preferred embodiment, dry spun layers suitable for use in the implants are made from P4HB and copolymers thereof. A suitable dry spun layer of micro-fibrous nonwoven for preparing an implant may be prepared by dissolving P4HB or copolymer thereof (weight average molecular weight from 50 kDa to 1,200 kDa) in chloroform, spinning the solution through a spinneret, and collecting the dry spun nonwoven. Further details of preparing suitable dry spun nonwoven made from P4HB and copolymers thereof for preparing the implants is described in US Patent Application No. 20120150285 to Cahil et al.

A suitable equipment set up for preparing electrospun microfiber outer layers for the implant comprises a reservoir of polymer solution, a pump for the polymer solution, a spinneret with numerous holes connected to a high voltage direct current, and a grounded collector plate. To prepare suitable electrospun microfiber layers, the polymer is dissolved in a solvent, the polymer solution pumped through the spinneret preferably under a constant pressure and flow rate, and the emerging polymer solution is charged by the electric field to form a jet of polymer material solution. As the charged jet of polymer moves towards the collector plate, the solvent is evaporated, and electrospun fiber is deposited at the collector plate to form a nonwoven microporous structure.

In a preferred embodiment, electrospun layers suitable for use in the implants are made from P4HB and copolymers thereof. A suitable electrospun layer of micro-fibrous nonwoven for preparing an implant may be prepared by dissolving P4HB or copolymer thereof (weight average molecular weight from 50 kDa to 1,200 kDa) in a solvent, for example chloroform, and pumping the polymer solution through a spinneret connected to a high voltage direct current so that charged jets of polymer (P4HB or copolymer thereof) exit the spinneret and a nonwoven is formed at a collector plate. The concentration of the polymer in the solvent is preferably 1 to 30 wt %, more preferably 5 to 10 wt %. Preferred solvents include methylene chloride, chloroform, dichloroethane, tetrachloroethane, trichloroethane, dibromethane, bromoform, acetone, acetonitrile, tetrahydrofuran, 1,4-dioxane, 1,1,1,3,3,3-hexafluoroisopropanol, toluene, xylene, dimethylformamide, dimethylsulfoxide, and mixtures thereof. Particularly preferred voltages for forming the electrospun nonwoven are 3-100 kV, more preferably 5-30 kV. The distance between the spinneret and the collector plate will depend upon the charge, spinneret dimensions, ejection volume, and polymer concentration. A distance of 5-30 cm is normally suitable when the electrostatic potential is close to 5-30 kV. A relative humidity of 20-80% is preferred, more preferably 30-70%. Further details of preparing suitable electrospun nonwoven from P4HB and copolymers thereof for preparing the implants is described in US Patent Application No. 20140277572 to Martin et al.

A particular advantage of using solvent-based processes such as dry spinning, centrifugal spinning, and electrospinning to prepare nonwovens of P4HB and copolymers thereof suitable for preparing the implants is that the nonwovens can be prepared with minimal loss of polymer weight average molecular weight. Typically, the loss of weight average molecular weight is less than 20%, more preferably between 0 and 10%.

Melt blown nonwoven suitable for preparing the implant may be prepared using high velocity air to blow hot extruded polymer from a die tip onto a conveyor or other collecting screen. A suitable equipment set up for preparing melt blown microfiber outer layers for the implant includes an extruder, metering pump, die assembly, hot air blower, and a collector. To prepare the melt blown nonwoven, molten polymer is conveyed to a melt blowing die using a screw extruder where it is extruded through many holes to create multiple polymer filaments. A stream of hot air is used to blow and attenuate the polymer filaments, and accelerate them towards the collector. At the collector plate, the polymer filaments may fuse if the filaments are still molten, or not fuse if the filaments have solidified very quickly after exiting the melt blowing die.

In a preferred embodiment, melt spun layers suitable for use in the implants are made from P4HB and copolymers thereof. A suitable melt spun layer of micro-fibrous P4HB nonwoven for preparing an implant may be prepared by feeding P4HB polymer (weight average molecular weight from 50 kDa to 600 kDa) into an extruder with a temperature range of 60-275° C., more preferably 80-240° C. The molten polymer is then fed into a melt-blowing die where the polymer is extruded through a spinneret with multiple holes, preferably on the order of 10-100 holes per inch. The extruded polymer filaments are then blown to a collector, preferably a moving collector, by heated high velocity air where the nonwoven is formed. The distance between the melt-blowing die and the collector is preferably 3-36 inches, and more preferably 8-27 inches. In a preferred method, the high velocity air is heated to 100-300° C., and more preferably to 180-240° C. The thickness of the nonwoven, density and fiber sizes can be controlled by varying a number of parameters, including, but not limited to, polymer weight average molecular weight, die configuration, hole spacing in the spinneret, number and size of the holes in the spinneret, temperature of the high velocity air, quenching temperature, distance between the die and collector, and the speed of travel of a moving collector screen. Further details of producing suitable melt blown nonwoven from P4HB and copolymers thereof for preparing the implants is described in US Patent Application No. 20090162276 to Martin et al.

In a preferred embodiment, the microporous nonwoven layers produced, for example, by spun laying, dry spinning, electrospinning and melt blowing, optionally from P4HB or copolymers thereof, have fibers with average diameters in the range of 100 nm to 20 µm, and more preferably 1 µm to 10 µm. In another preferred embodiment, the microporous nonwoven layers produced, for example, by spun laying, dry spinning, electrospinning and melt blowing, optionally from P4HB or copolymers thereof, have average pore size diameters of less than 10 µm, and more preferably 0.5 µm to 10 µm. In a further embodiment, the microporous nonwoven layers produced, for example, by spun laying, dry spinning, electrospinning and melt blowing, optionally from P4HB or copolymers thereof, have a thickness between 5 µm and 100 µm.

It is generally preferred that the microporous layers of the implant are made from one or more resorbable polymers, and degrade in 1 to 6 months. Implants can be made, for example, from polyglycolic acid if fast resorption of the microporous layers is required. Implants with somewhat slower degrading microporous layers can be made, for example, from copolymers of glycolic and lactic acid, or from polydioxanone. In a particularly preferred embodiment, the microporous layers of the implant can be made from unoriented P4HB fibers. The rate of degradation of the P4HB fibers may be further controlled by selecting the weight average molecular weight of the polymer. When slower degrading implants are required, P4HB with weight average molecular weight of 350 to 600 kDa can be used, and P4HB with weight average molecular weight of 50 to 349 kDa can be used when faster degradation is required. Incorporating smaller diameter P4HB fibers into the microporous layer will also result in more rapid degradation of the implant. For example, unoriented P4HB fibers with diameters of 1 to 100 µm may degrade in 1-3 months whereas unoriented P4HB fibers with diameters over 100 µm may degrade in 3-6 months or more. In a preferred embodiment, the microporous layers have P4HB fibers with one or more of the following properties: (i) weight average molecular weight between 50 and 349 kDa; (ii) fiber diameters between 1 to 100 µm; and (iii) no orientation or partial orientation, preferably so the fibers have an elongation to break between 50% and 1,000%. For reference purposes, an unoriented P4HB fiber has an elongation to break of 1,000%. In another embodiment, the microporous layers have P4HB fibers with one or more of the following properties: (i) weight average molecular weight between 350 and 600 kDa; (ii) fiber diameters between 101 and 250 µm; and (iii) unoriented or partially oriented P4HB fibers, preferably P4HB fibers with an elongation to break between 50% and 1.000%.

E. Macroporous Filler

The implant may optionally comprise one or more fibrous structures, including layers such as a nonwoven, or loose fiber structure, that is macroporous inside the fillable reservoir of the implant. Suitable macroporous fiber structures can be produced, for example, by knitting, melt spinning or wet spinning fiber, including production of macroporous nonwoven fiber structures by spun laying and melt blowing. A particularly preferred method of producing the macroporous fiber filler is by spun laying.

The macroporous filler may be produced from the polymers listed in Section II.A. The macroporous fillers are preferably made from resorbable polymers.

In a preferred embodiment, the average fiber diameters of the macroporous fibers that can be used inside the fillable reservoir of the implant, optionally made from P4HB and copolymers thereof, are 10 µm to 250 µm, and more preferably 20 µm to 50 µm. In another preferred embodiment, the average pore size diameters of the macroporous fiber structures, or macroporous inner layers, that can be used inside the fillable reservoir of the implant, optionally made from P4HB and copolymers thereof, are 75 µm to 5 mm, and more preferably 100 µm to 500 µm.

In one embodiment, suitable spunlaid macroporous fiber may be produced from P4HB (weight average molecular weight of 50 kDa to 600 kDa) using extrusion temperatures of 60° C. to 250° C., more preferably 80° C. to 230° C. and even more preferably maximum extrusion temperatures of 210-230° C., and a vacuum system with an air flow rate ranging from between 40 and 220 cu ft/min (1.13-6.23 m$^3$/min). In a preferred embodiment, the P4HB spunlaid macroporous fiber structure is prepared by cooling the extruded filaments at a temperature between 4° C. and 30° C., more preferably from 15° C. to 25° C. to allow fiber surface crystallization and minimize fiber-to-fiber melt adhesion. In another preferred embodiment, the P4HB spunlaid macroporous fiber may be heated using a post-collection air stream at a temperature between 30° C. and 58° C. more preferably between 42° C. and 52° C., in order to soften the P4HB fibers and make them tacky to obtain improved cohesion of the fibers in the spunlaid. In a preferred embodiment, the P4HB macroporous fibrous structure has one or more of the following properties: (i) unoriented fibers or partially oriented fibers with elongation to break values between 50 and 1,000%; (ii) average fiber diameters of 10 μm to 250 μm; (iii) polymer fiber weight average molecular weight from 50 kDa to 600 kDa, more preferably 50 kDa to 350 kDa; and (iv) average pore size of >75 microns to 5 mm.

III. Methods of Manufacturing Implants with Fillable Reservoirs

A variety of methods can be used to manufacture the implants.

Figure 1:
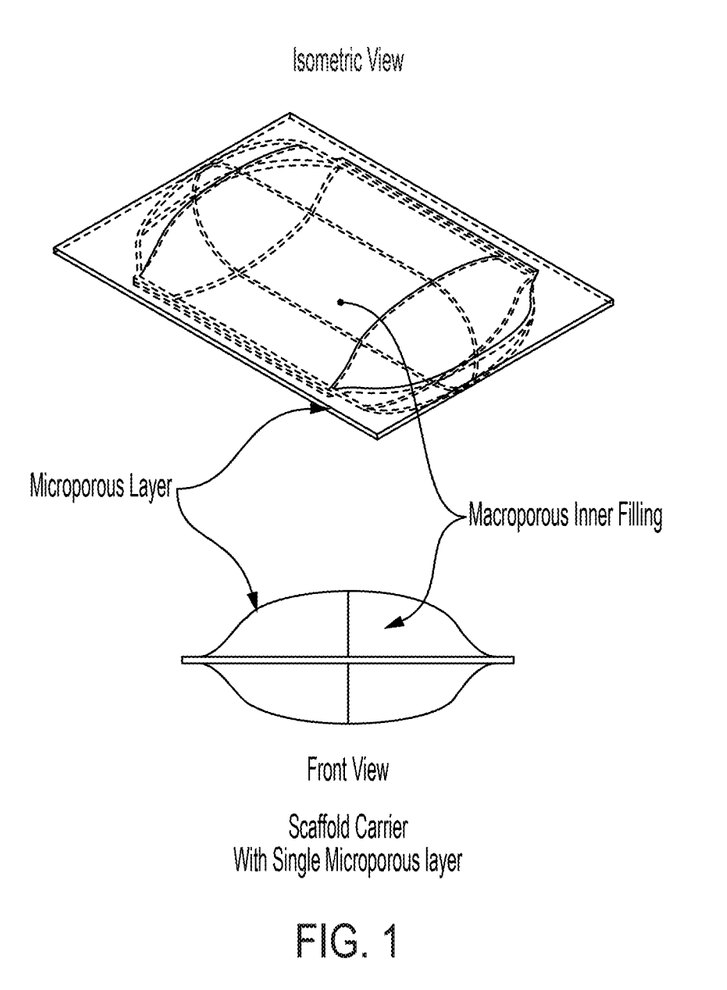
FIG. 1 is a diagram showing isometric and cross-sectional views of an implant that comprises an outer microporous layer with sealed edges, and a fillable reservoir. The diagram shows the location where fiber forming a macroporous structure may be placed.
Figure 2:
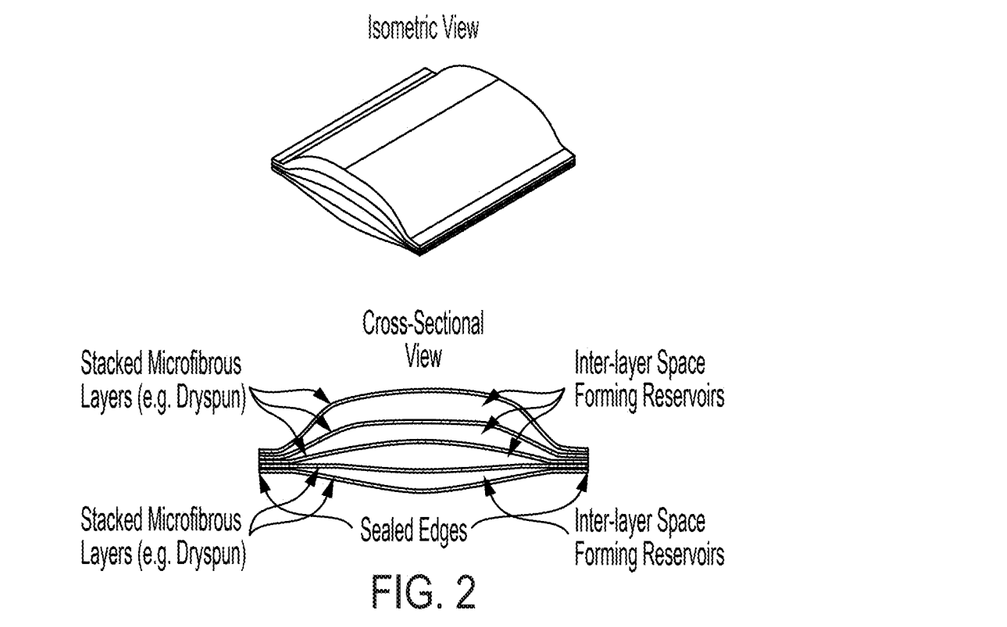
FIG. 2 is a diagram showing isometric and cross-sectional views of an implant that comprises multiple fillable reservoirs made by sealing together the edges of multiple microfibrous layers stacked on top of each other.

In one embodiment, an implant with a fillable reservoir is prepared from two microporous layers by placing one layer on top of the other layer, and sealing their edges together as shown in FIG. 1. The edges may be sealed together to form a fillable reservoir between the microporous layers, for example, by using a calendering system wherein a heated bar or a roll of heated bars is pressed against the edges of the two microporous layers in order to seal them together. In another alternative method, the edges of the two microporous layers may be sealed together using ultrasonic welding bars. If desired, the implant may comprise additional microporous layers, and comprise multiple fillable reservoirs as shown in FIG. 2. These implants may also be prepared by stacking microporous layers on top of each other, and sealing their edges together as shown in FIG. 2. As described above, the microporous layers may be prepared, for example, by spun laying, dry spinning, electrospinning, and melt blowing. The microporous layers may be made from the same material or from different materials, or by the same technique or different techniques. For example, microporous layers made from fast and slow resorbing polymers can be incorporated into the implant. Or, a microporous layer coated with a bioactive substance may be combined with other microporous layers that do not contain bioactive substances. Or, for example, a microporous layer made by spun laying can be combined in an implant with a microporous layer made with a dry spun, melt blown or electrospun microporous layer, or any combinations of spun laid, dry spun, electrospun and melt spun layers combined in an implant. A particularly preferred polymer for preparing the implants shown in FIGS. 1 and 2 is P4HB and copolymers thereof.

Figure 3:
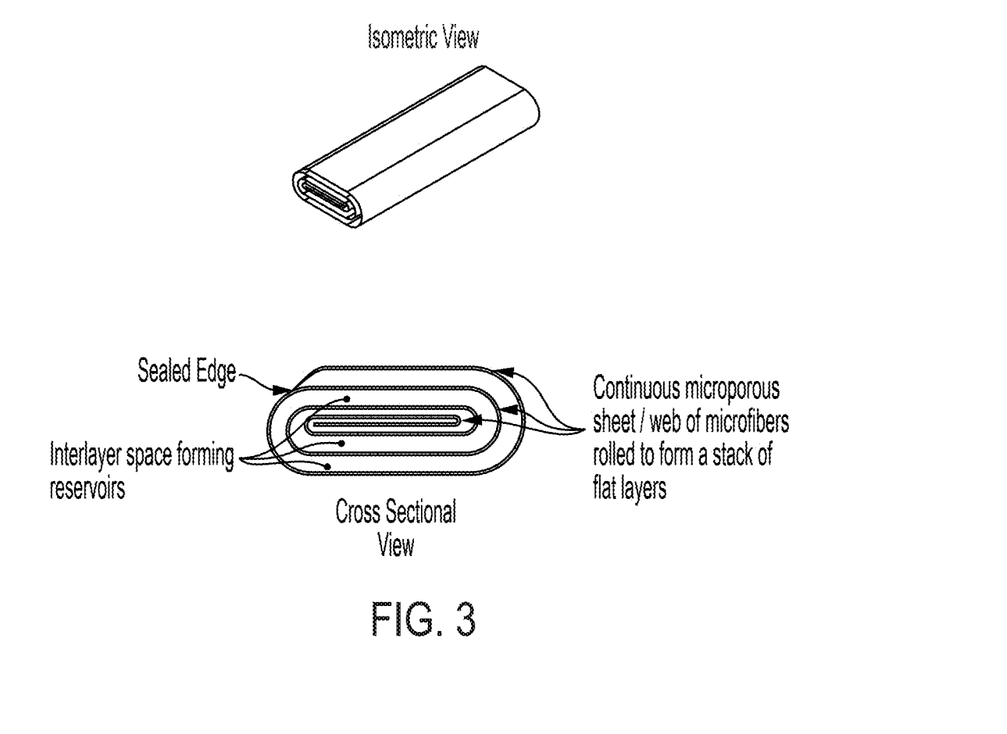
FIG. 3 shows isometric and cross-sectional views of an implant prepared by wrapping a microporous layer around a flat substrate that is mounted on a mandrel. The cross-sectional view shows the reservoir formed between the microporous layers, and sealing of the outer edge.

In another embodiment, an implant with one or more fillable reservoirs may be prepared by wrapping a microporous layer around a flat substrate that has been placed on a mandrel as shown in FIG. 3. Parallel layers of the microporous substrate are formed as the mandrel is rotated, as shown in the cross-sectional view of FIG. 3. By sealing the edges of the microporous layer, an implant is formed with a reservoir between the layers of the microporous nonwoven. The distance between the microporous layers, which in turn determines the capacity of the reservoir, can be controlled by applying more or less tension to the microporous layer while it is being rotated about the flat substrate. Preferably, the microporous layers are prevented from wrinkling, and structural failure, as they are wrapped around the flat substrate by keeping them flat. Driving rollers and sprockets can be used for this purpose. In a preferred embodiment, a tension of 10-200 cN/cm is applied to the microporous layer during wrapping. A particularly preferred polymer for preparing the implant shown in FIG. 3 is P4HB and copolymers thereof.

The implants, when used in rhinoplasty procedures, should preferably have a fillable reservoir or reservoirs with a capacity of between 0.1 and 3 cc, more preferably at least 0.2 cc, and even more preferably between 0.2 cc and 3 cc. The implants, when used in ear reconstruction should preferably have a fillable reservoir or reservoirs with a capacity of the reservoir or reservoirs between 0.1 and 2 cc. The implants, when used in breast reconstruction or soft tissue repair should preferably have a fillable reservoir or reservoirs with a capacity of the reservoir or reservoirs between 10 and 150 cc. The implants may be designed and constructed so that the reservoir or reservoirs expand upon filling.

In a preferred embodiment, the implants further comprise fiber filler that forms a macroporous structure, including a nonwoven. The macroporous fiber structure can help provide a reservoir for augmentation materials, particularly fluid augmentation materials, including microfat, fat, fat extracts, collagen, DCF, gels, hydrogels, cells, stem cells, as well as bioactive agents. Preferably, the macroporous fiber filler structure helps the implant when used in a rhinoplasty procedure retain up to one cc of fluid volume. In a preferred embodiment, the ratio of the volume of the implant occupied by the microporous outer layers, and optionally the fibers of the macroporous structure, to the total volume of the implant is between 0.05 and 20%, and more preferably between 0.1-2%.

Figure 4:
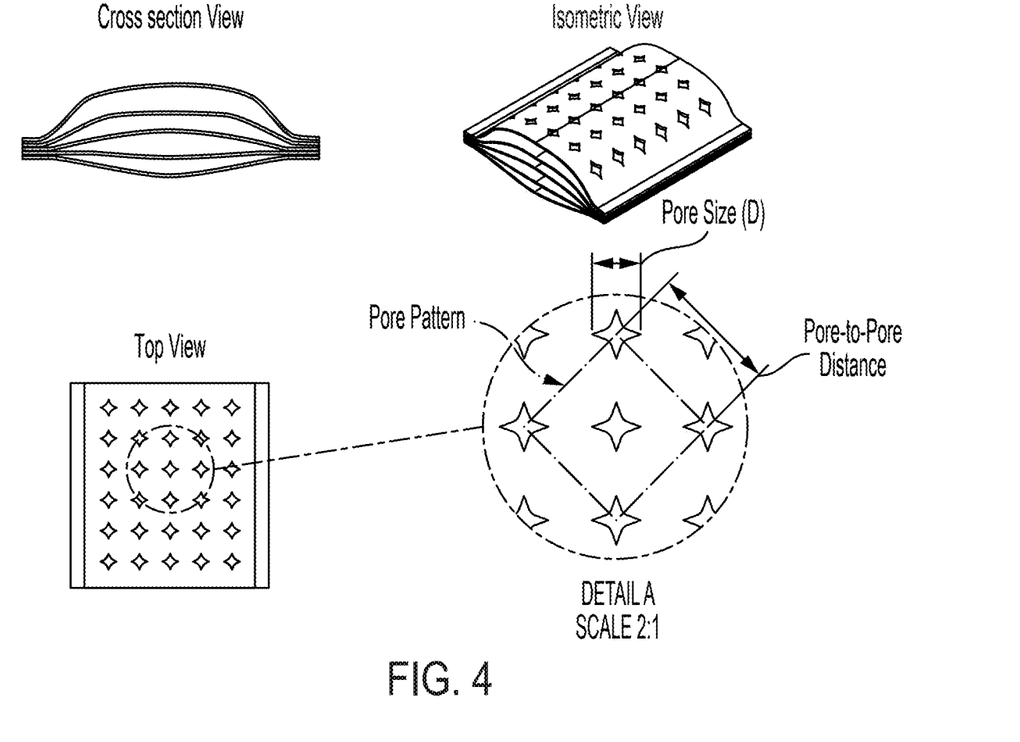
FIG. 4 is a diagram showing cross-sectional, isometric and top views of an implant that comprises multiple microporous layers with macropores visible in the outermost layer.

In another embodiment, the implants may comprise one or more macropores in the microporous layers. For example, the implants shown in FIGS. 1-3 may contain one or more macropores. Macropores are desirable in implants that comprise thicker microporous layers, and in particular when the overall thickness of the implant is 0.4 mm or more. Placing macropores in thicker microporous layers (e.g. of 0.4 mm of more) allows better cell ingrowth by facilitating diffusion of oxygen, nutrients, and waste products to support and maintain viable tissue. The size of the one or more macropores may range from 0.0045 mm$^2$ to 5 mm$^2$, and is more preferably between 0.25 mm$^2$ and 4 mm$^2$. Preferably, the macropores have a minimum diameter of 75 μm. In the event the implant further comprises thermal bonding points, the macropores are preferably located at least 5 mm away from the thermal bonding points. The macropores may have any shape, such as circular, triangular and diamond shapes, and the same or different shapes within an implant. A circular shape is preferred to maintain better mechanical integrity. FIG. 4 shows an example of the rhinoplasty implant (shown in FIG. 2) that has been perforated with macropores. The macropores may be inserted in the microporous layers by any suitable means, including mechanical punching and cutting with a laser.

Figure 5:
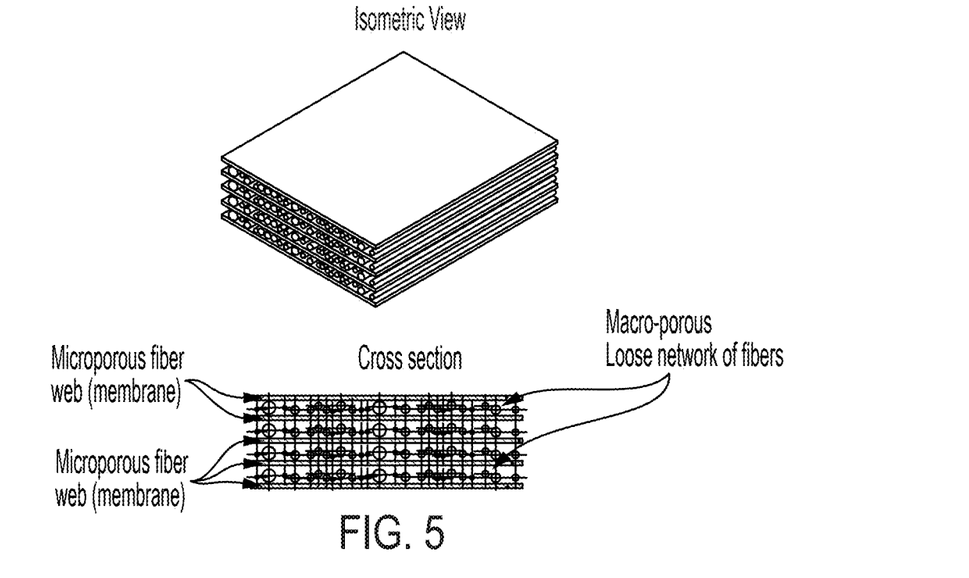
FIG. 5 is a diagram showing isometric and cross-sectional views of a rhinoplasty implant that comprises fillable reservoirs formed by alternating layers of microporous nonwoven and fibers forming macroporous structure.

In a further embodiment, an implant with a fillable reservoir can be prepared by alternating layers of microporous nonwoven with layers of macroporous fiber structure as shown in FIG. 5, and sealing the edges of the layers as described above. In this embodiment, the implant has at least one layer of macroporous fiber structure wrapped and sealed by an outer layer of a microporous nonwoven membrane. In a preferred embodiment, the implant comprises 2 to 20 microporous layers and 1 to 19 macroporous fiber layers that alternate with the microporous layers, with the exterior of the implant consisting of a microporous layer.

Figure 6:
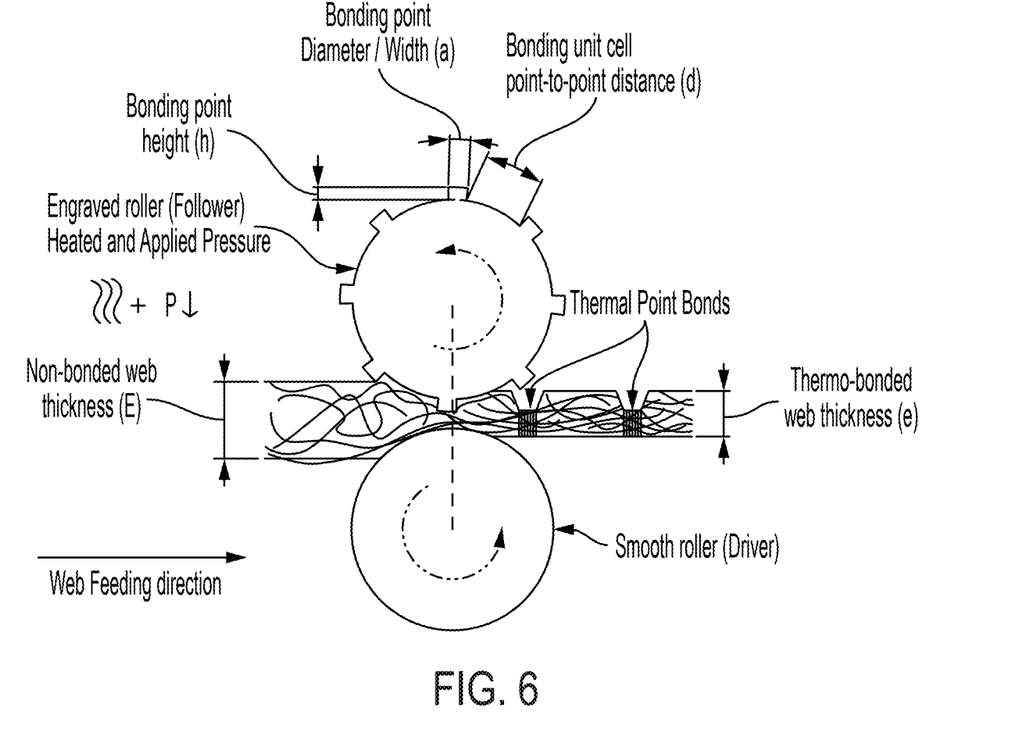
FIG. 6 is a diagram showing the use of an engraved calender roll and a smooth calender roll to thermally point-bond an implant.

In a particularly desired embodiment, the implants are thermally point-bonded. Thermal point-bonding of the implants increases the strength of the implant, and can prevent delamination of layers incorporated into the implant. The implants are thermally point-bonded by applying heat and pressure at discrete points, for a period of time, and preferably using a calender. A preferred method to thermally point-bond an implant using an engraved calender roll and a smooth calender roll is shown in FIG. 6. The depth and dimensions (e.g. diameter or width) of the point-bonds, and the distance between point-bonds can be controlled by varying the positions and sizes of the protrusions engraved on the calender roll, as well as process conditions such as roller diameter, pressure in the roller gap, speed of the structure to be point-bonded through the calendering rolls, and the roller temperature, as shown in FIG. 6. In a particularly preferred embodiment, the implant is made from P4HB or copolymer thereof, and is thermally point-bonded.

Figure 8:
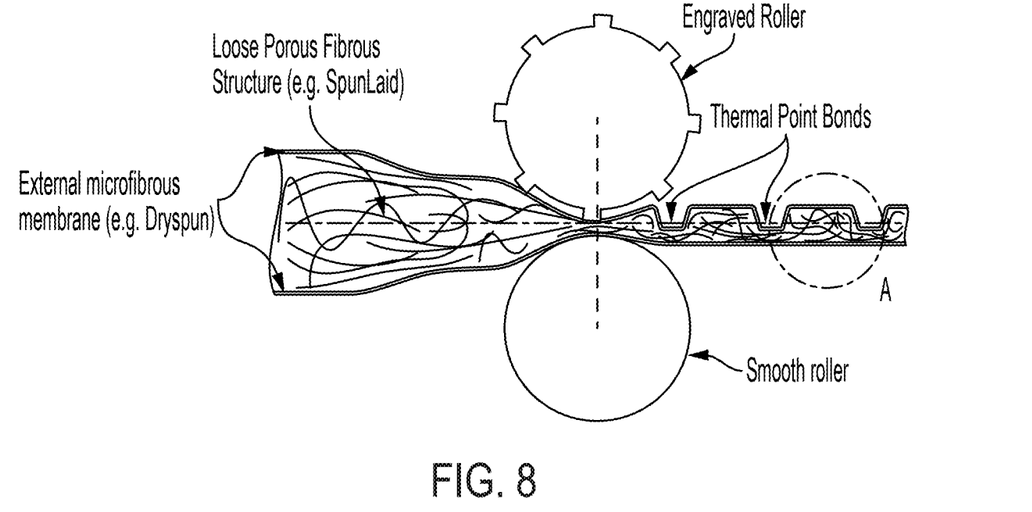
FIG. 8 is a diagram showing the manufacture of a thermally point-bonded implant with an outer microporous nonwoven layer and an inner macroporous layer of fibers. Area "A" is shown in more detail in FIG. 7.
Figure 9:
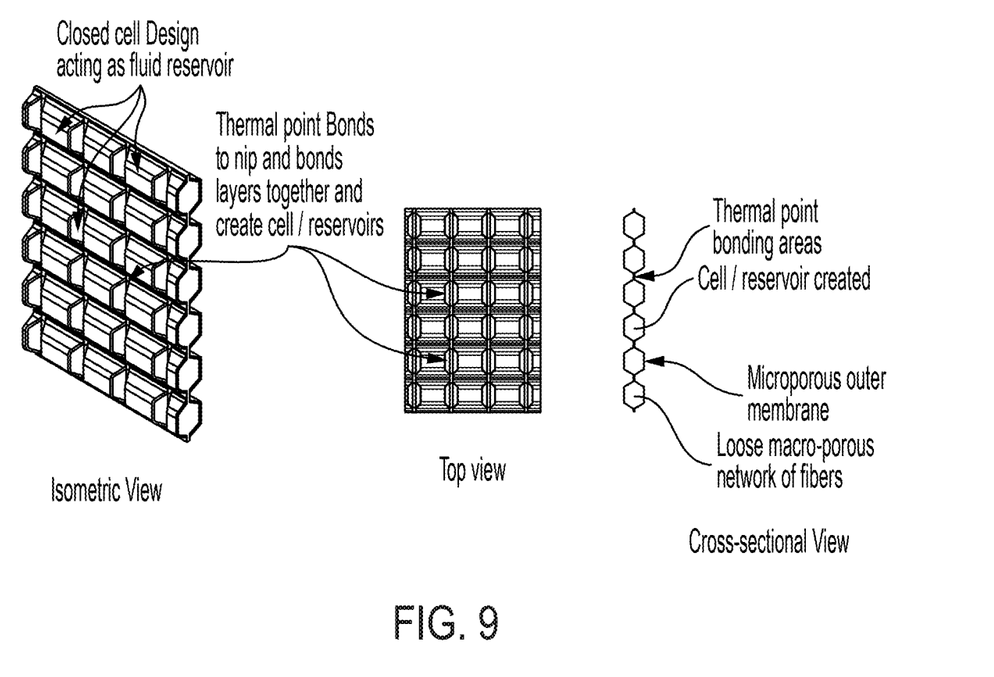
FIG. 9 is a diagram showing an isometric view, a top view and a cross-section view of a thermally point-bonded implant with a fillable reservoir made from a network of interconnected unit cells which optionally contain loose fiber forming a macroporous structure. The outer layer of the implant is made from a microporous nonwoven.

A cross-sectional view showing in more detail a fillable reservoir of an implant formed by the process of thermal point-bonding is shown in FIG. 7. The implant comprises an external outer microporous nonwoven layer and a macroporous inner layer of fiber, and is part of an interconnected network of unit cells comprising a microporous outer layer and a macroporous fiber inner layer. FIG. 8 shows the manufacture of the unit cell shown in FIG. 7 (see area "A"). FIG. 9 shows the design of an implant with an interconnected network of unit cells creating a fillable reservoir that can be prepared by thermal point-bonding. The implant comprises an external microporous layer, and optionally can be filled with loose fibrous material forming a macroporous structure. The implant may be cut and shaped to size. In a particularly preferred embodiment, the implant is prepared from P4HB or copolymer thereof.

Figure 10:
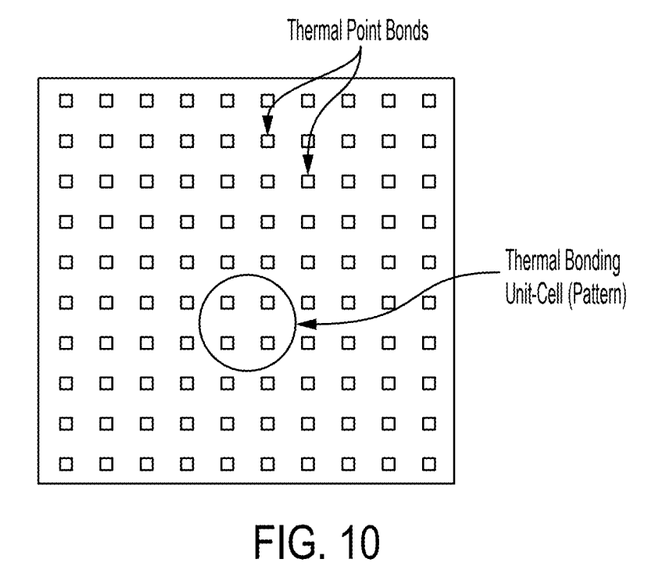
FIG. 10 is a diagram showing a pattern of thermal bonding points, and a unit cell created by thermal bonding, that can be used to prepare an implant with a fillable reservoir.
Figure 11:
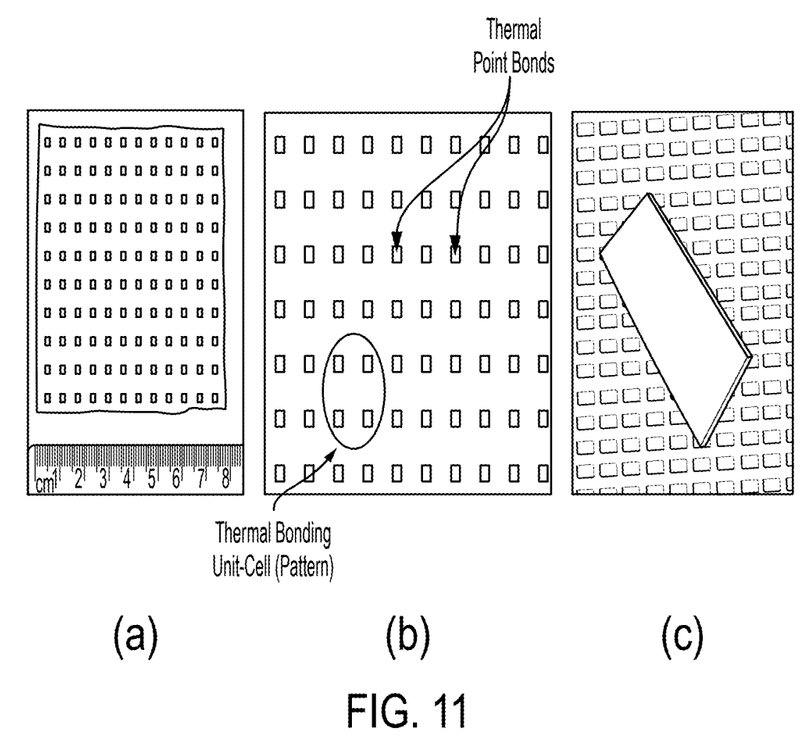
FIG. 11 shows pictures of (a) thermal pointed-bonded P4HB implant with a fillable reservoir made from dry spun and spun laid fibers, (b) a magnification of picture 11(a) showing the square design of the bond points of the thermally point-bonded implant, and (c) a 1.5 cm×3.5 cm rhinoplasty implant that has been filled with 0.8 cc of human microfat.

An example of a P4HB implant that has been thermally point-bonded with the pattern shown in FIG. 10 is shown in FIG. 11. The implant comprises dry spun and spunlaid layers that have been thermally point-bonded. FIG. 11(a) shows the point-bonded implant with a fillable reservoir after thermal point-bonding. FIG. 11(b) is a magnified picture of the implant showing the square pattern of thermal point bonds in the P4HB implant. FIG. 11(c) shows a 1.5 cm×3.5 cm rhinoplasty implant prepared from the implant of FIG. 11(a) wherein the implant's fillable reservoir has been filled with 0.8 cc of human microfat using a needle and syringe.

The minimum tensile strength of the implant should be high enough to maintain the integrity of the implant during preparation of the implant and placement at the implantation site. The implant should have sufficient strength to prevent it from unraveling and fraying, yet be easy for the surgeon to cut. In an embodiment, the implants prepared as described herein should have a minimum tensile strength of 0.5 N/cm, and a maximum tensile strength of 50 N/cm. In another embodiment, the implant should have a minimum burst strength of 1 N/cm$^2$, and a maximum burst strength of 40 N/cm$^2$. In a preferred embodiment, the implant comprises P4HB or copolymer thereof, and has one or more of the following properties: a tensile strength between 1 N/cm and 20 N/cm, a suture pullout strength of 0.1 to 100 N, and more preferably 1 to 25 N, and a burst strength between 2 N/cm$^2$ and 25 N/cm$^2$.

IV. Methods of Implanting

The implants may be used in rhinoplasty procedures, for example to (i) improve aesthetic appearance of the patient's nose; (ii) restore structure and shape following trauma; (iii) correct abnormalities of the nose; and (iv) correct functional problems of the nasal passage to improve breathing. The implants may be used alone or in combination with other techniques to alter underlying nasal structures such as bone, cartilage, ligaments and soft tissue. The implants may be used to create or preserve certain proportions between various parts of the nose and face in order to restore or maintain functionality, remediate structural issues, and address aesthetic factors. The implants may be used in open, closed or minimally invasive rhinoplasty procedures, and may be used in primary or secondary rhinoplasty procedures. The implants may be cut and shaped for specific procedures, and are preferably fixated in place, for example, using sutures and more preferably absorbable sutures.

Preferably, the reservoirs of the implants are filled with microfat, fat, fat extracts, cells, diced cartilage, or other biological material prior to implantation, but the implants can be used without filling their reservoirs. Augmentation materials used to fill the reservoirs may be autografts, allografts, xenografts or other biological or synthetic materials. Particularly preferred materials are microfat and DCF. Any suitable method can be used to fill the reservoir of the implant; however, a preferred method is to use a syringe and needle.

In an embodiment, the implants may be used to augment the nose dorsum (build up the bridge of the nose). The implants may be used to treat patients with collapsed or flat noses, or to change the appearance of a relatively low bridge, common in certain ethnic groups, to a more projected, pronounced or "Western" profile. For these procedures, it is preferable, but not essential, that the size of the implant is 1.5 cm×3.0 cm. In a preferred method to augment the dorsum, the implant is filled with diced cartilage fascia (DCF) or other augmentation material such as microfat. DCF may be obtained, for example, from cartilage of the rib, ear, or septum. The cartilage is chopped into very small pieces, typically about 0.5 to 1 mm cubes. To augment the dorsum, the DCF is placed inside the fillable reservoir of the implant, and the implant is inserted onto the dorsum. The implant may be secured at the implantation site using sutures or by another suitable fixation method.

In other embodiments, the implant may be used to modify the nasal tip, for example, to improve nasal tip projection. The implant may be grafted onto the intermediate crura to accentuate the nasal tip, or be used as a columellar strut, including a septal extension graft, for example, to lengthen a short nose. In another embodiment, the implant may be used as a caudal septal extension graft, for example, to support the nasal tip, prevent postoperative loss of tip projection, or set nasal length. In further embodiments, the implant may be fixated to alar cartilage, for example, as a shield graft, or used as a spreader graft or middle vault augmentation graft, for example, to increase middle vault width, improve symmetry, increase the airway or straighten the dorsum septum. The implant may also be used to lengthen the nose, or provide that appearance, for example by placing implants on the caudal aspect of the alar domes.

Although it is intended that a significant use of the implants will be in rhinoplasty procedures, the implants may be used in other surgical procedures, including other plastic surgery procedures and general surgery procedures. For example, the implants may be used in reconstruction of the ear. In this case, it is desirable that the size of the implant is 3 cm×6 cm. The implants may also be used as a substitute for a TRAM (transverse rectus abdominis myocutaneous) flap, for example, to reconstruct a breast or other tissue. In this case, the size of the implant is preferably 10 cm×20 cm. The implants may also be placed subcutaneously in the upper pole of the breast to create volume.

The present invention will be further understood by reference to the following non-limiting examples.

Example 1: Manufacture of an Implant with a Fillable Reservoir and Macroporous Fiber Filler Microporous P4HB dry spun (Mw=250 kDa) was prepared by solution spinning an 8% solution of P4HB in chloroform through a 1.0 mm annular spinneret (1.1 mm inner diameter and 2.1 mm outer diameter) to yield a dry spun nonwoven with a thickness of 162 microns, density of 4.5 mg/cm$^2$, and fiber diameter of 3.9±4.3 μm. A macroporous spunlaid P4HB nonwoven was prepared by melt extrusion of P4HB (Mw=460 kDa) using a maximum temperature of 247° C. through a die with spinneret hole diameters of 150 μm and temperature of 20-25° C., attenuating the filaments, and collecting the P4HB filaments on a moving belt. The formed macroporous spunlaid structure had a fiber size ranging from 19 to 64 μm, areal density of 18±4 mg/cm$^2$ an average thickness of 1.6±0.4 mm, and an average pore size (diameter) of 413±219 μm. The implant was then formed by thermal point bonding of a sandwich structure comprising outer layers of P4HB microporous dry spun with an inner layer of loose macroporous spunlaid P4HB fibers at a temperature of 63° C. The bonding point geometry used was 1×1 mm squares. Bonding points were in a diamond pattern and were 6.5 mm apart. Prior to implantation, the implant was filled with 0.8 cc of micro fat (extracted from human fat by centrifugation) using an 18-gauge needle and 1 cc syringe.

Example 2: Manufacture of an Implant with a Fillable Reservoir, No Macroporous Fiber Filler Structure, and Laser Cut Macropores Eight layers of the microporous P4HB dry spun prepared in Example 1 were stacked on top of each other, and thermally point bonded as described in Example 1 (with the same pattern). A laser was then used to cut diamond patterned macropores in the implant that had a size of 1 mm×2 mm.

Figure 12:
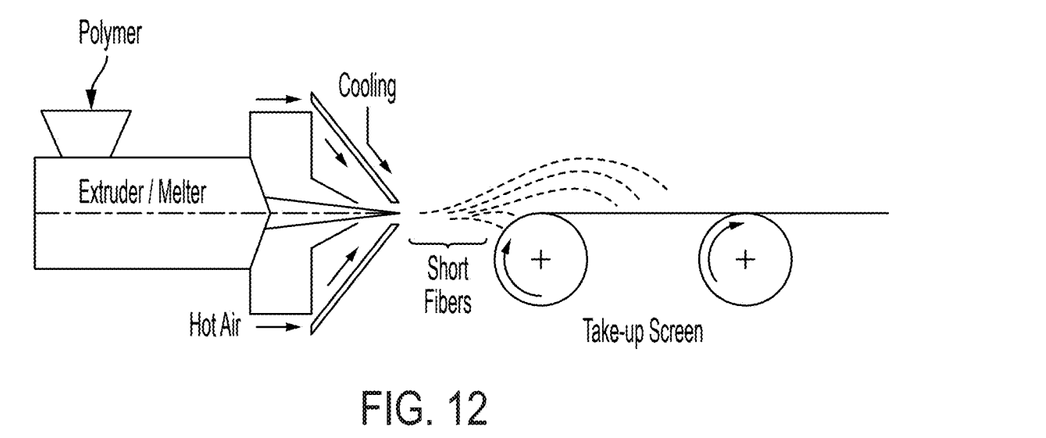
FIG. 12 is a diagram showing a suitable equipment set up for preparing melt-blow P4HB.

Example 3. Manufacture of an Implantable Fillable Reservoir Made of Nonwoven Felt Sandwiched Between Two Layers of Melt-Blown Needle punched P4HB multifilament was formed into a nonwoven felt of 2-4 mm thickness and placed between two P4HB melt-blown layers. The melt-blown was prepared using the equipment set up shown in FIG. 12, and conditions shown in Table 1, from P4HB pellets which were dried under vacuum overnight to less than 0.01% (w/w) water content. The equipment used for melt blowing consisted of a 6" melt-blowing die fed by a 1" single screw extruder. The die was configured with 120 holes of 0.010" diameter, 3:1 L/D. The die tip was set back 0.060" from the face of the die and had a 0.060" air gap. A melt temperature of about 230° C., and air temperature of 230° C. provided a good web of P4HB fibers. The speed of the belt collector was varied to collect P4HB melt-blown non-wovens of various thicknesses as shown in Table 2. An implant with a fillable reservoir was prepared from a composite structure of the needle punched P4HB nonwoven felt and the melt-blown by quilt spot bonding the layers using thermal energy, and the edges of the sandwiched layers were thermally sealed.

TABLE 1

Conditions for melt-blowing P4HB Polymer prepared in Example 3

| Extruder | | | | | Ambient | Die | | | Attenuation Air | | | |
|---|---|---|---|---|---|---|---|---|---|---|---|---|
| Zone 1 Deg C. | Zone 2 Deg C. | Zone 3 Deg C. | Connector Deg C. | Speed RPM | Air Temp Deg C. | Zone 2 Deg C. | Zone 3 Deg C. | Zone 4 Deg C. | Press. PSI | Press. PSI | Temp. Deg C. | DCD mm |
| 144.7 | 202.9 | 234 | 229.7 | 2 | 33.5 | 248.3 | 228.4 | 238.5 | 700 | 3 | 230 | 630 |

TABLE 2

Properties of P4HB melt-blown prepared in Example 3

| Sample | | Thickness, | Unit Weight, | Ball Burst, |
|---|---|---|---|---|
| Roll # | Sample # | mm | gm/m2 | KGF |
| 1 | 10 | 0.166 | 64.6 | 2.9 |
| 2 | 5 | 0.114 | 38.5 | 1.5 |

Example 4. Manufacture of an Implantable Fillable Reservoir Made of a Knitted P4HB Mesh Sandwiched Between Two Layers of P4HB Microporous Felt Microporous P4HB felt was made by needle punching a loose web of unoriented P4HB fibers (Mw=300 kDa) with a diameter range of 50 to 165 microns. Needle punching was performed using 11 needles per inch to produce a felt with an average thickness of 1.2 mm, and an average areal density of 280 g/m$^2$. The average pore size of the needle punched P4HB felt was 120 microns. A macroporous P4HB layer was produced by knitting size 5-0 oriented P4HB monofilaments (Mw=340 kDa) in a diamond pattern with an average pore size of 320 microns and an average areal density of 132 g/m$^2$. The diamond knitted mesh was sandwiched between two layers of the P4HB needle punched felt, and the layered structure was then placed over a 5 cm×5 cm aluminum anvil with a diamond welding pattern. The composite was welded with round bonding points having a 0.13 mm diameter, placed 6.35 mm deep and 6.35 mm apart using a 3-inch circular horn driven and bonded using a Branson 2000X ultrasonic unit. The ultrasonic welding energy used was 10 Joules, with a hold time of 0.3 seconds, and an amplitude of 80% and a pressure of 30 psi (206 kPa).

Figure 13:
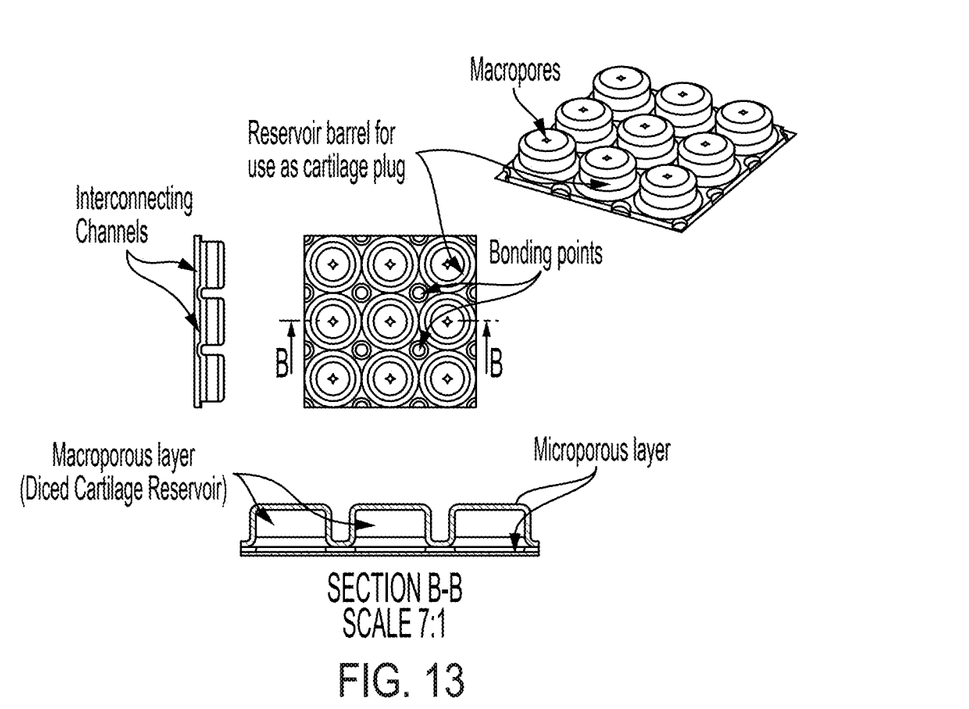
FIG. 13 shows views of an implant, suitable for use as a meniscus plug, that comprises an outer microporous layer and a fillable reservoir containing macroporous material. The diagram shows the locations where the microporous and macroporous layers have been bonded together to form barrel-like reservoirs that may be filled, for example, with diced cartilage.

Example 5. Manufacture of an Implantable Fillable Reservoir Made of Microporous and Macroporous Layers for Use as a Meniscus Plug An implant with a fillable reservoir was prepared by sandwiching a macroporous layer of P4HB spunlaid between outer layers of microporous P4HB dryspun, and thermally point bonding the construct to form barrel-like reservoirs as shown in FIG. 13. The layers were thermally point bonded at 63° C. for 15 seconds to produce the barrel-like reservoirs with an average diameter of 4 mm and an average height of 5 mm as shown in FIG. 13. A square bonding pattern with 5 mm spacing and 1 mm circular point bonds was used. Prior to implantation, the implant was filled with 0.3 cc of diced cartilage with average chunk size of 0.5 mm using a 12-gauge needle and 1 cc syringe. The filled construct was then cut to size using a 6 mm round punch with the cartilage-loaded reservoir at the center.

Example 6. Manufacture of an Implantable Fillable Reservoir Made of a P4HB Hollow Braid Coated with a Thin Microporous Layer An implant with a fillable reservoir was prepared by braiding 6-0 monofilament P4HB fibers (average fiber diameter of 100 μm) using a 12-carrier braiding machine, 1×1 pattern, diamond pore shape, and an 8 mm diameter round core. The braid along with the core was cut in 12 in long (30.48 cm) sections placed on a wire mandrel and rotated at 12 rpm. The same dry spinning setup and parameters described in Example 1 were used to deposit a thin layer (average thickness of 84 μm) of microporous P4HB dry spun over the rotating braid. Upon completion, the inner core was removed from the coated braid, and the coated braid was sealed and cut into 4 cm long sections using a 1 centimeter wide impulse sealer and a pair of scissors. The resulting structure was a barrel-like reservoir with sealed top and bottom ends. The sides of the reservoir consisted of a loose macroporous braided inner layer with an average 0.9 mm pore size and an outer microporous layer composed of dry spun P4HB. The reservoir can be filled with about 2 cc of diced cartilage using a 10 gauge syringe and needle.

Modifications and variations of the methods and compositions will be apparent from the foregoing detailed description and are intended to come within the scope of the appended claims.

We claim:

1. A method of forming an implant with a fillable reservoir, the implant configured to allow tissue ingrowth, the method comprising acts of:
   (a) forming a fillable reservoir comprising one or more microporous outer layers and a macroporous structure of fibers located within the fillable reservoir formed by the one or more microporous outer layers, the fillable reservoir formed by:
   (i) forming an interconnected network of unit cells by thermal point bonding the one or more microporous outer layers and the macroporous structure, or
   (ii) sealing edges of the one or more microporous outer layers with the macroporous structure located within the fillable reservoir.

2. The method of claim 1, wherein the implant further comprises additional microporous layers within the implant.

3. The method of claim 1, wherein the one or more microporous outer layers comprise nonwovens and have a thickness between 1 and 100 μm.

4. The method of claim 1, wherein: (i) a thickness of the unit cells is between 0.4 mm and 4.0 mm; (ii) a surface area of the unit cells of the fillable reservoir is at least 4 mm$^2$, but less than 150 mm$^2$ or (iii) a size of at least one macropore of the macroporous structure is between 0.0045 mm$^2$ and 5 mm$^2$.

5. The method of claim 1, wherein the implant is configured for use in: (i) rhinoplasty and the fillable reservoir has a capacity when filled of between 0.1 and 3 cc; and/or the implant has a length of 0.2 to 3.0 cm, and the implant has a breath of 0.1 to 1.5 cm, (ii) ear reconstruction and the capacity of the fillable reservoir when filled is between 0.1 and 2 cc and/or the length of the implant is 1 to 3 cm, and the breath of the implant is 3 to 6 cm, and (iii) breast reconstruction or soft tissue repair and the capacity of the fillable reservoir when filled is between 10 and 150 cc and/or the length of the implant is 5 to 10 cm, and the breath of the implant is 10 to 20 cm.

6. The method of claim 1, wherein a ratio of a volume of the implant occupied by the one or more microporous outer layers and the macroporous structure inside the fillable reservoir relative to a total volume of the implant is between 0.1 and 20%.

7. The method of claim 1, further comprising filling the fillable reservoir with one or more of the following: fat, microfat, fat extracts, cartilage, diced cartilage with fascia, cells, stem cells, gels, hydrogels, dermis, collagen, and bioactive agent.

8. The method of claim 1, further comprising reinforcing an inside of one or more of the unit cells.

9. The method of claim 1, wherein the one or more microporous outer layers of the implant acts as a wick, and help to prevent loss of fluid from the fillable reservoir.

10. The method of claim 1, wherein the implant is resorbable.

11. The method of claim 1, wherein the implant comprises one or more of the following polymers or copolymers: polymers or copolymers comprising glycolic acid, lactic acid, D-lactic acid, L-lactic acid, 1,4-dioxane, trimethylene carbonate, 3-hydroxybutyrate, 4-hydroxybutyrate, and ε-caprolactone; polyhydroxyalkanoate; polyester; polycarbonate; polyurethane; polyamide; tyrosine polycarbonate; polyesteramide; polyether; polyvinylpyrrolidone; polyacetal; polyetherester; polyphosphate; polyphosphoester; polyalkylene succinate; polyalkylene alkylate; polycyanoacrylate; polyketal; polyalkylene oxalate; polymaleic acid; silk; chitin; chitosan; collagen; and polysaccharide.

12. The method of claim 1 further comprising an additive or bioactive agent.

13. The method of claim 12, wherein the additive or bioactive agent is selected from one or more of the following: plasticizer, nucleant, compatibilizer, porogen, absorbable polymer, natural polymer, synthetic polymer, growth factor, fibroblast growth factor, transforming growth factor, platelet derived growth factor, epidermal growth factor, granulocyte-macrophage colony stimulating factor, vascular endothelial growth factor, insulin-like growth factor, hepatocyte growth factor, interleukin-1-B, interleukin-8, nerve growth factor, cellular differentiating factor, cellular recruiting factor, cell receptor, cell-binding factor, cell signaling molecule, cytokines, molecules to promote cell migration, molecules to promote cell division, molecules to promote cell proliferation, molecules to promote extracellular matrix deposition, hormone, antimicrobial, antibiotic, bacitracin, biguanide, trichlosan, gentamicin, minocycline, rifampin, vancomycin, cephalosporins, copper, zinc, silver, and gold, disinfectant, oncological agent, anti-scarring agent, peptide, protein, cell adhesion factor, fibronectin, vitronectin, laminin, elastin, fibrinogen, collagen type I, collagen type II, collagen type V, antibody, lipid, polysaccharide, hyaluronic acid, hyaluronic acid derivatives, chitosan, alginate, low molecular weight compound, steroid, vitamin, analgesic, anesthetic, immunomodulatory agent, blood clotting agent, wetting agent, polymers of ethylene oxide, polymers of propylene oxide, nucleic acid molecules, DNA, RNA, siRNA, miRNA, antisense nucleic acids, aptamers, anti-angiogenic factor, pro-angiogenic factor, platelet rich plasma, and anti-inflammatory agent.

14. The method of claim 1, wherein the one or more microporous outer layers include at least one macropore.

15. The method of claim 1, wherein act (a)(ii) includes sealing the edges of the one or more microporous outer layers by calendaring.

16. The method of claim 3, wherein the nonwovens are prepared by spun laying, dry spinning, and electrospinning.

17. The method of claim 4, wherein the surface area of the unit cells of the fillable reservoir is less than 100 mm$^2$.

18. The method of claim 4, wherein the size of the at least one macropore is between 0.25 mm$^2$ and 4 mm$^2$.

19. The method of claim 5, wherein the implant is configured for use in rhinoplasty and the fillable reservoir has a capacity when filled of between 0.5 and 2 cc.

20. The method of claim 6, wherein the ratio of the volume of the implant occupied by the one or more microporous outer layers the macroporous structure inside the fillable reservoir relative to the total volume of the implant is between 1 to 10%.

* * * * *